US012788987B2

(12) United States Patent
Chang et al.

(10) Patent No.: US 12,788,987 B2
(45) Date of Patent: Nov. 10, 2026

(54) ELECTRICAL STIMULATION METHOD, ELECTRICAL STIMULATION DEVICE, EXTERNAL CONTROL DEVICE, AND COMPUTER-READABLE STORAGE MEDIUM

(71) Applicant: GIMER MEDICAL. Co. LTD., New Taipei City (TW)

(72) Inventors: Chi-Heng Chang, New Taipei City (TW); Jian-Hao Pan, New Taipei City (TW); Mei-Ching Wang, New Taipei City (TW); Wei-Tso Lin, New Taipei City (TW); Chan-Yi Cheng, New Taipei City (TW)

(73) Assignee: COFORCE MEDICAL CO., LTD., Taipei City (TW)

( * ) Notice: Subject to any disclaimer, the term of this patent is extended or adjusted under 35 U.S.C. 154(b) by 840 days.

(21) Appl. No.: 17/981,596

(22) Filed: Nov. 7, 2022

(65) Prior Publication Data

US 2023/0201595 A1 Jun. 29, 2023

(30) Foreign Application Priority Data

Dec. 29, 2021 (CN) ......................... 202111638880.1

(51) Int. Cl.
*A61N 1/36* (2006.01)

(52) U.S. Cl.
CPC ........ *A61N 1/36128* (2013.01); *A61N 1/3603* (2017.08); *A61N 1/36139* (2013.01)

(58) Field of Classification Search
CPC .............. A61N 1/36128; A61N 1/3603; A61N 1/36139
See application file for complete search history.

(56) References Cited

U.S. PATENT DOCUMENTS

| | | | | |
|---|---|---|---|---|
| 10,632,307 B2 * | 4/2020 | Parker | ................ | A61N 1/36139 |
| 2006/0052856 A1 * | 3/2006 | Kim | .................. | A61N 1/36071 607/117 |

(Continued)

FOREIGN PATENT DOCUMENTS

| | | |
|---|---|---|
| TW | 200824742 A | 6/2008 |
| TW | M487094 U | 10/2014 |

(Continued)

OTHER PUBLICATIONS

Taiwanese Office Action and Search Report for Taiwanese Application No. 111134825, dated Apr. 26, 2023.

*Primary Examiner* — Lindsey G Wehrheim
(74) *Attorney, Agent, or Firm* — Birch, Stewart, Kolasch & Birch, LLP

(57) ABSTRACT

An electrical stimulation method is provided. The electrical stimulation method is applied to an electrical stimulation device and an external control device. The electrical stimulation method includes the following steps. The predetermined electrical stimulation level that corresponds to the predetermined target energy is obtained by the external control device. The predetermined target energy is one of the target energies in the first target energy set. The external control device selects the target energy upper bound and the target energy lower bound from the first target energy set according to the predetermined electrical stimulation level. The external control device generates a second target energy set according to the target energy upper bound and the target energy lower bound. The electrical stimulation device performs electrical stimulation of the target area of a target object according to the second target energy set.

21 Claims, 7 Drawing Sheets

(56) References Cited

U.S. PATENT DOCUMENTS

| | | | | |
|---|---|---|---|---|
| 2010/0010590 A1* | 1/2010 | Skelton | .................. | G16H 40/63<br>607/62 |
| 2019/0134403 A1* | 5/2019 | Steinke | ............. | A61N 1/37247 |

FOREIGN PATENT DOCUMENTS

| | | | |
|---|---|---|---|
| TW | 201632223 | A | 9/2016 |
| TW | 201827010 | A | 8/2018 |

* cited by examiner

ELECTRICAL STIMULATION METHOD, ELECTRICAL STIMULATION DEVICE, EXTERNAL CONTROL DEVICE, AND COMPUTER-READABLE STORAGE MEDIUM

CROSS REFERENCE TO RELATED APPLICATIONS

This Application claims priority of China Patent Application No. 202111638880.1, filed on Dec. 29, 2021, the entirety of which is incorporated by reference herein.

BACKGROUND

Technology Field

The present disclosure relates in general to electrical stimulation techniques, and it relates in particular to electrical stimulation techniques for generating a set of new target energies according to a predetermined electrical stimulation level.

Description of the Related Art

In recent years, dozens of kinds of therapeutic electrical nerve stimulation devices have been developed, and tens of thousands of people undergo implant surgery with electrical stimulation devices every year. Due to developments in precision manufacturing technology, medical instruments such as implantable electrical stimulation devices have been shrunk so that they can be implanted into the human body.

Conventionally, there are usually a plurality of electrical stimulation levels for users to select on the operating interface of the external control device that controls the electrical stimulation device. Each of the electrical stimulation levels may correspond to different target energies. However, not all of the target energies set by default will be therapeutically effective and comfortable for the patient. Therefore, finding out what the most suitable target energy is for electrical stimulation of the patient is a crucial issue.

SUMMARY

In view of the problems of the prior art described above, an electrical stimulation method, an electrical stimulation device, an external control device, and a computer-readable storage medium are provided in the embodiments of the present disclosure.

An electrical stimulation method is provided according to an embodiment of the present disclosure. The electrical stimulation method is applied to an electrical stimulation device and an external control device. The electrical stimulation method includes the following steps. The method includes obtaining a predetermined electrical stimulation level using the external control device. The predetermined electrical stimulation level corresponds to a predetermined target energy, which is one of the target energies in the first target energy set. The method includes selecting a target energy upper bound and a target energy lower bound from the first target energy set according to the predetermined electrical stimulation level using the external control device. The method includes generating a second target energy set according to the target energy upper bound and the target energy lower bound using the external control device. The method includes performing electrical stimulation on the target area of a target object according to the second target energy set using the electrical stimulation device.

An electrical stimulation device is provided according to an embodiment of the present disclosure. The electrical stimulation device is applied to perform electrical stimulation. The electrical stimulation device may include a controller. The controller is used for obtaining a predetermined electrical stimulation level. The predetermined electrical stimulation level corresponds to a predetermined target energy, and the predetermined target energy is one of the target energies in the first target energy set. The controller selects a target energy upper bound and a target energy lower bound from the first target energy set according to the predetermined electrical stimulation level, and the controller generates a second target energy set according to the target energy upper bound and the target energy lower bound. Additionally, the controller performs electrical stimulation on the target area according to the second target energy set.

An external control device is provided according to an embodiment of the present disclosure. The external control device is applied to perform electrical stimulation. The external control device may include a controller. The controller is used for obtaining a predetermined electrical stimulation level. The predetermined electrical stimulation level corresponds to a predetermined target energy, and the predetermined target energy is one of the target energies in the first target energy set. The controller selects a target energy upper bound and a target energy lower bound from the first target energy set according to the predetermined electrical stimulation level, and the controller generates a second target energy set according to the target energy upper bound and the target energy lower bound. Additionally, the external control device transmits the second target energy set to an electrical stimulation device, and the electrical stimulation device performs electrical stimulation on the target area according to the second target energy set.

A computer-readable storage medium is provided according to an embodiment of the present disclosure. The computer-readable storage medium stores one or more instructions, and cooperates with an electrical stimulation device and an external control device. When the instructions are executed by the electrical stimulation device, the electrical stimulation device and the external control device execute the following steps. The predetermined electrical stimulation level is obtained. The predetermined electrical stimulation level corresponds to the predetermined target energy, which is one of the target energies in the first target energy set. The target energy upper bound and the target energy lower bound are selected from the first target energy set according to the predetermined electrical stimulation level. The second target energy set is generated according to the target energy upper bound and the target energy lower bound. Electrical stimulation is performed on the target area according to the second target energy set.

It will be apparent to those skilled in the art that various modifications and variations can be made in the present disclosure, without departing from the spirit and scope of the present disclosure.

BRIEF DESCRIPTION OF THE DRAWINGS

The present disclosure can be more fully understood by reading the subsequent detailed description and examples with references made to the accompanying drawings, wherein.

DETAILED DESCRIPTION OF THE INVENTION

The following description is a preferred embodiment of the invention, which is intended to describe the basic spirit of the invention, but is not intended to limit the invention. For the actual inventive content, reference must be made to the scope of the claims.

Figure 1:
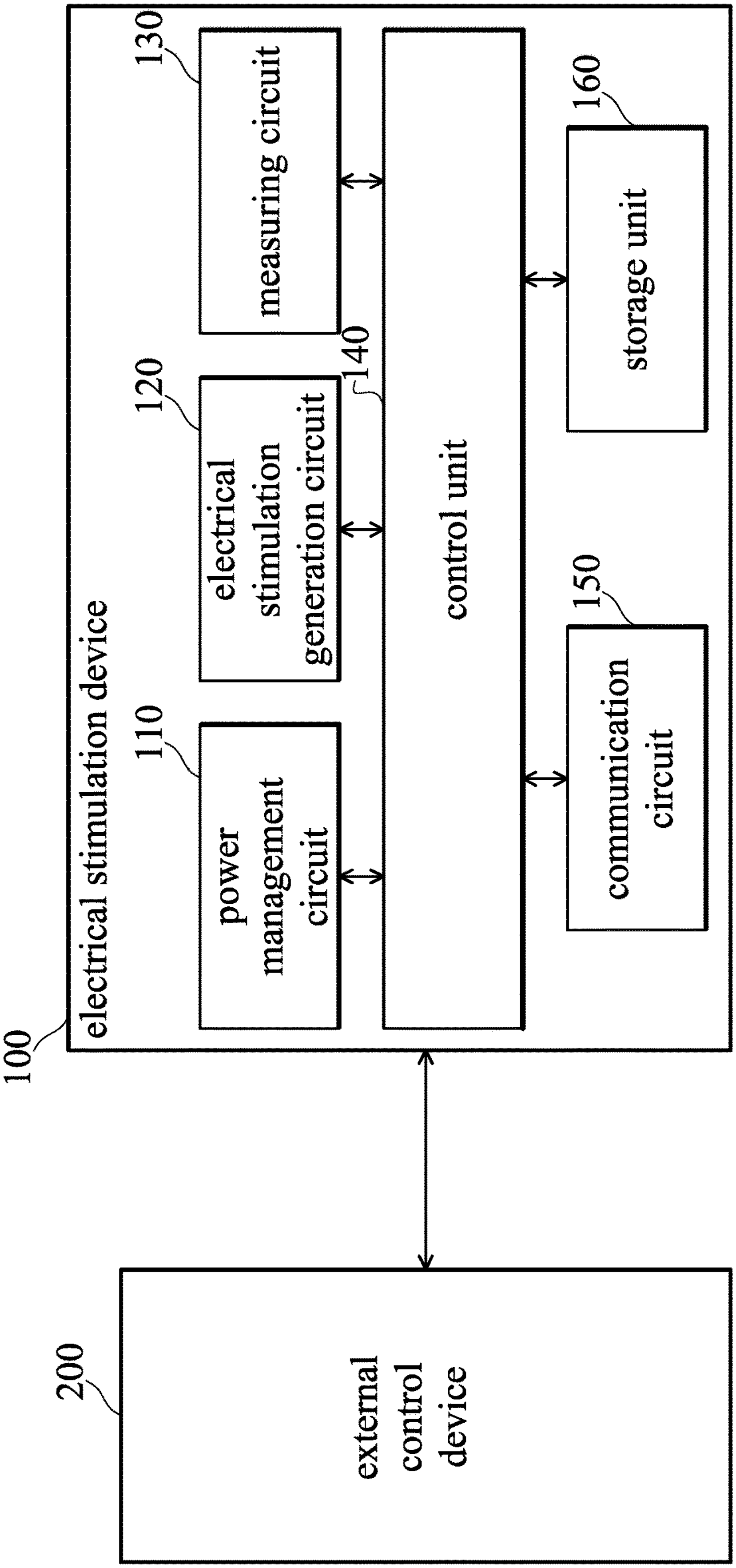
FIG. 1 is a block diagram of an electrical stimulation device, according to an embodiment of the present disclosure.

FIG. 1 is a block diagram of an electrical stimulation device 100, according to an embodiment of the present disclosure. As shown in FIG. 1, the electrical stimulation device 100 at least includes a power management circuit 110, an electrical stimulation generation circuit 120, a measuring circuit 130, a control unit 140, a communication circuit 150, and a storage unit 160. It should be appreciated that the block diagram shown in FIG. 1 is only for the convenience of explaining the embodiments of the present disclosure, the present disclosure is not limited thereto. The electrical stimulation device 100 may also include other elements.

According to an embodiment of the present disclosure, the electrical stimulation device 100 may be electrically coupled to an external control device 200. The external control device 200 may be provided with an operation interface. According to user's operation on the operation interface, the external control device 200 may generate instructions or signals to be transmitted to the electrical stimulation device 100, and transmits the instructions or signals to the electrical stimulation device 100 via a wire communication (e.g., a transmission line).

In addition, according to another embodiment of the present disclosure, the external control device 200 may transmit the instructions or signals to the electrical stimulation device 100 via a wireless communication, such as Bluetooth, Wi-Fi, or NFC (near field communication).

According to the embodiment of the present disclosure, the electrical stimulation device 100 may be an implantable electrical stimulation device, an external electrical stimulation device with a lead implanted into human body, or a transcutaneous electrical nerve stimulation device (TENS). According to an embodiment of the present disclosure, when the electrical stimulation device 100 is a non-implantable electrical stimulation device (e.g., an external electrical stimulation device or a transcutaneous electrical nerve stimulation device), the electrical stimulation device 100 may be integrated with the external control device into a device. According to an embodiment of the present disclosure, the electrical stimulation device 100 may be an electrical stimulation device with batteries, or an electrical stimulation device of which power is transmitted wirelessly by the external control device 200. According to an embodiment of the present disclosure, in a trial phase, the electrical stimulation device 100 is an external electrical stimulation device with a lead implanted into human body. There are electrodes on the lead, so that the external electrical stimulation device may send the electrical stimulation signal to the corresponding target area via the electrodes on the lead. In the trial phase, after the terminal of the lead with electrodes has been implanted into the human body, the other terminal of the lead is thereby linked to the external control device 200, and the external stimulation device may send an electrical stimulation signal to evaluate the effectiveness of the therapy, and to confirm if the functions of the lead are normal, and if the position into which the lead is implanted is correct. In the trial phase, the external control device 200 may first pair with the external electrical stimulation device (i.e., a non-implantable electrical stimulation device). After the lead is implanted into the human body, the external electrical stimulation device may be connected to the lead. The external electrical stimulation device may be wirelessly controlled by the external control device 200 to perform electrical stimulation of the human body. According to an embodiment of the present disclosure, if the evaluation in the trial phase is effective, a permanent implantation phase may be entered. In the permanent implantation phase, the electrical stimulation device 100 is implanted into the human body together with the lead. The electrical stimulation device 100 sends the electrical signal to the corresponding target area via the electrodes on the lead. While the external control device 200 is entering the permanent implantation phase, a user or a doctor must let the external control device 200 detect a phase change card, so as to change the state of the external control device 200 from the trial phase to the permanent implantation phase via near field wireless communication. In addition, the external control device 200 may select a target energy upper bound and a target energy lower bound from the first target energy set according to a predetermined electrical stimulation level. Then, the external control device 200 may generate the second target energy set according to the target energy upper bound and the target energy lower bound (further explanation will be provided). Moreover, before the permanent implantation phase or during the permanent implantation phase, the external control device 200 may pair with the implantable electrical stimulation device first, and the external electrical stimulation device (i.e., a non-implantable electrical stimulation device) may be removed, and the electrical stimulation device 100 (i.e., an implantable electrical stimulation device) connects to the lead and is implanted into the human body.

According to the embodiment of the present disclosure, the power management circuit 110 is used for providing power to the elements and circuit in the electrical stimulation device 100. The power provided by the power management circuit 110 may be from a built-in rechargeable battery, or the external control device 200, but the present disclosure is not limited thereto. The external control device 200 may provide power to the power management circuit 110 using a wireless power technology. The power management circuit 110 may be activated or deactivated according to the instructions of the external control device 200. According to an embodiment of the present disclosure, the power management circuit 110 may include a switch circuit (not shown in the figure). The switch circuit may be switched on or off according to the instructions of the external control device 200, so as to activate or deactivate the power management circuit 110.

According to the embodiment of the present disclosure, the electrical stimulation signal generation circuit 120 is used for generating the electrical stimulation signal. The electrical stimulation device 100 may transmit the generated electrical stimulation signal to the electrodes on the lead via at least a conductor, so as to perform electrical stimulation on the target area of the body of a user (human or animal) or a patient. The target area may be, for example, spine, spinal nerve, vagus nerve, trigeminal nerve, lateral recess, or peripheral nerve, but the present disclosure is not limited thereto. The detailed structure regarding the electrical stimulation signal generation circuit 120 will be explained in FIG. 4.

Figure 2A:
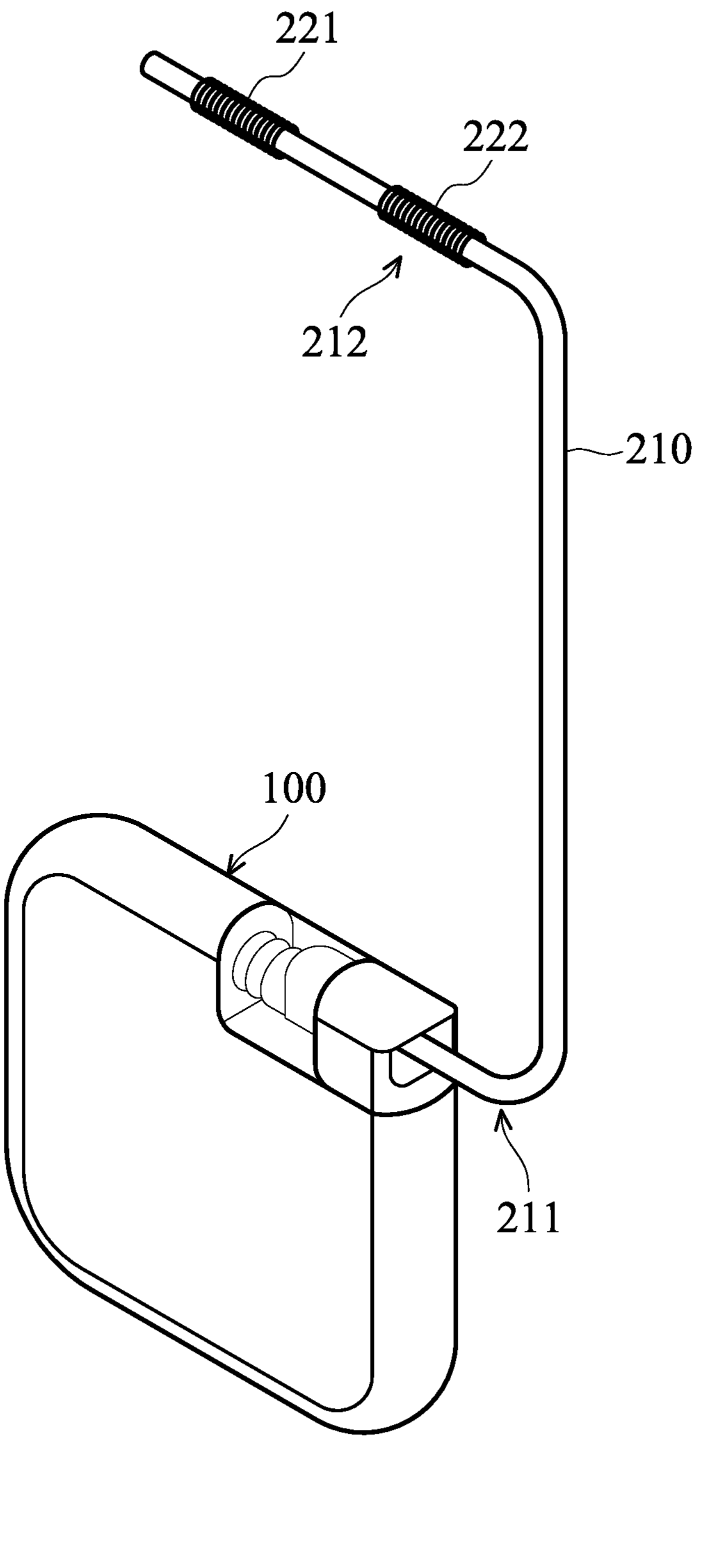
FIG. 2A is a schematic diagram of an electrical stimulation device, according to an embodiment of the present disclosure.

FIG. 2A is the schematic diagram of an electrical stimulation device 100, according to an embodiment of the present disclosure. As shown in FIG. 2A, the electrical stimulation signal may be output to the lead 210, so that the electrical stimulation signal may be transmitted via a terminal 211 of the lead 210 to the other terminal 212 of the lead 210. In an embodiment of the present disclosure, the electrical stimulation device 100 and the lead 210 may be separately electrically connected to each other, but the present disclosure is not limited thereto. For example, the electrical stimulation device 100 and the lead 210 may be a monolithic device.

Figure 2B:
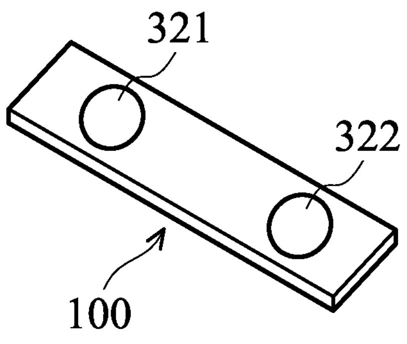
FIG. 2B is a schematic diagram of an electrical stimulation device, according to another embodiment of the present disclosure.

FIG. 2B is the schematic diagram of an electrical stimulation device 100, according to another embodiment of the present disclosure. As shown in FIG. 2B, the electrode 321 and the electrode 322 may be directly installed on one side of the electrical stimulation device 100. The electrical stimulation signal may be transmitted to the electrode 321 or the electrode 322, so as to perform electrical stimulation on the target area. In other words, in this embodiment, the electrical stimulation device 100 does not need to transmit the electrical stimulation signal to the electrode 321 and the electrode 322 via the lead.

Figure 3:
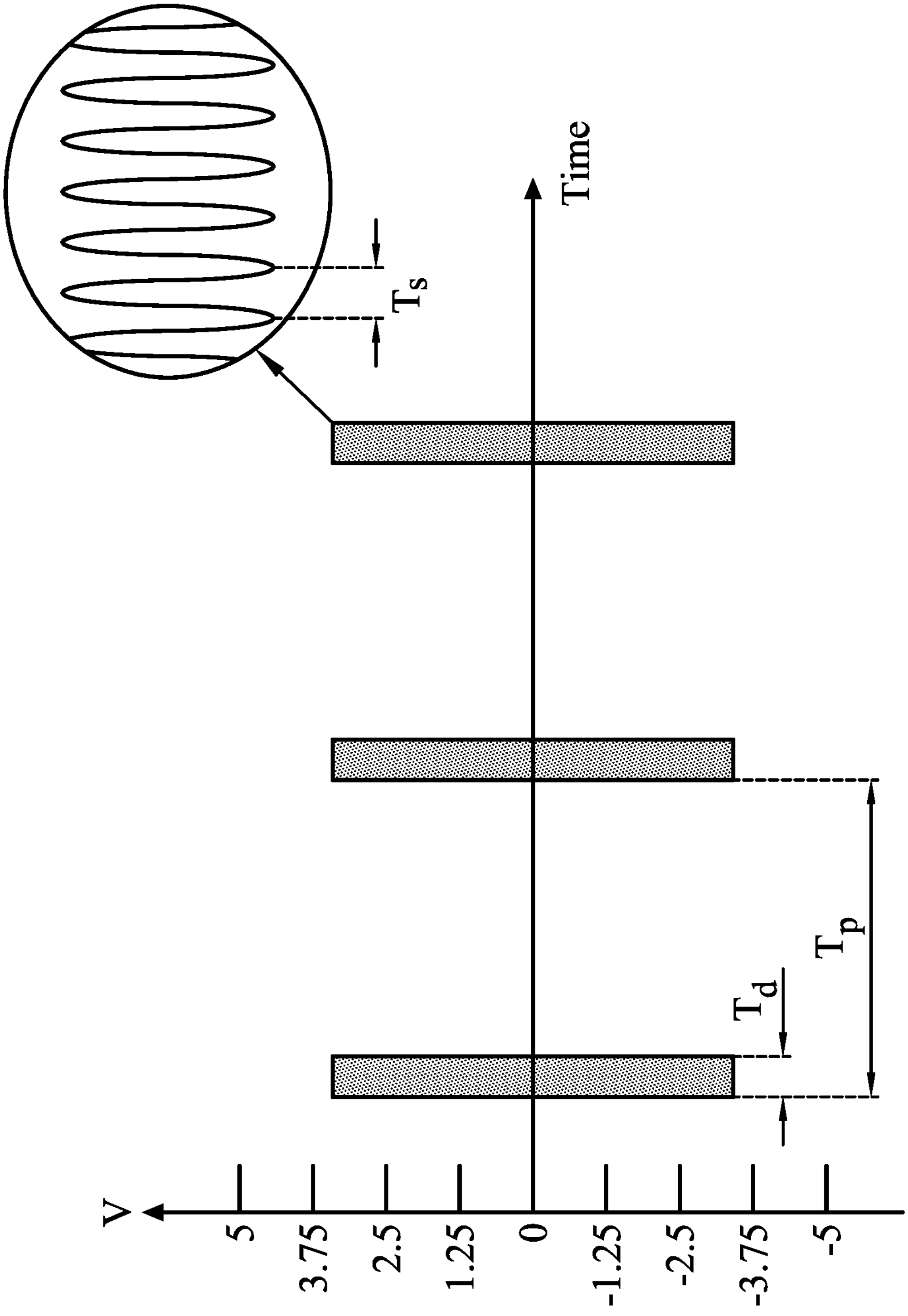
FIG. 3 is a waveform diagram of the electrical stimulation signals of the electrical stimulation device, according to an embodiment of the present disclosure.

FIG. 3 is the waveform diagram of the electrical stimulation signals of the electrical stimulation device, according to an embodiment of the present disclosure. As shown in FIG. 3, according to an embodiment of the present disclosure, the electrical stimulation signal may be a pulsed radiofrequency (PRF) signal (also referred to as a pulse signal, for short), a continuous sinusoidal waveform, or a continuous triangle waveform, but the present disclosure is not limited thereto. Besides, when the electrical stimulation signal is a pulse AC (alternating current) signal, a pulse cycle time $T_p$ includes a pulse signal and at least an idle period, and the pulse cycle time $T_p$ is the inverse of the pulse repetition frequency. For example, the pulse repetition frequency (also referred to as the pulse frequency, for short) may ranges from 0 Hertz to 1K Hertz, preferably range from 1 Hertz to 100 Hertz. In this embodiment, the exemplary pulse repetition frequency of the electrical stimulation signal is 2 Hertz. Besides, the duration time $T_d$ (i.e., the pulse width) of a pulse in a pulse cycle time may be at 1-250 milliseconds, preferably at 10-100 milliseconds. In this embodiment, the exemplary duration time $T_d$ is 25 milliseconds. In this embodiment, the frequency of the electrical stimulation signal is 500K Hertz. In other words, the electrical stimulation signal cycle time $T_s$ is approximately 2 microseconds (μs). In addition, the frequency of the electrical stimulation signal is the intra-pulse frequency in each pulse AC signal of FIG. 3. In some embodiments, the intra-pulse frequency of the electrical stimulation signal may, for example, range from 1K Hertz to 1000K Hertz. It should be appreciated that in each embodiment of the present disclosure, the frequency of the electrical stimulation signal refers to the intra-pulse frequency of the electrical stimulation signal. Furthermore, the intra-pulse frequency of the electrical stimulation signal may, for example, range from 200K Hertz to 800K Hertz. Furthermore, the intra-pulse frequency of the electrical stimulation signal may, for example, range from 480K Hertz to 850K Hertz. Furthermore, the intra-pulse frequency of the electrical stimulation signal may be, for example, 500K Hertz. The voltage of the electrical stimulation signal may range from −25V~+25V. Furthermore, the voltage of the electrical stimulation signal may range from −20V~+20V. The current of the electrical stimulation signal may range from 0-60 mA. Furthermore, the current of the electrical stimulation signal may range from 0-50 mA.

According to an embodiment of the present disclosure, a user may operate the electrical stimulation device 100 to perform electrical stimulation only when in need (e.g., the symptom becomes more serious or does not alleviate). After the electrical stimulation device 100 has performed electrical stimulation on the target area once, the electrical stimulation device 100 must wait for a limited period before performing electrical stimulation on the target area again. For example, after the electrical stimulation device 100 has performed electrical stimulation on the target area once, the electrical stimulation device 100 must wait for 30 minutes (i.e., the limited period) before performing electrical stimulation on the target area again, but the present disclosure is not limited thereto. The limited period may be 45 minutes, 1 hour, 4 hours, or any time period within 24 hours.

According to the embodiment of the present disclosure, the measuring circuit 130 may measure the voltage value and the current value of the electrical stimulation signal according to the electrical stimulation signal generated by the electrical stimulation signal generation circuit 120. In addition, the measuring circuit 130 may measure the voltage value and the current value on the tissues in the target area of the body of the user or the patient. According to an embodiment of the present disclosure, the measuring circuit 130 may adjust the current and the voltage of the electrical stimulation signal according to the instructions of the control unit 140. The detailed structure regarding the measuring circuit 130 will be explained in FIG. 4.

According to the embodiment of the present disclosure, the control unit 140 may be a controller, a microcontroller, or a processor, but the present disclosure is not limited thereto. The control unit 140 may be used for controlling the electrical stimulation signal generation circuit 120 and the measuring circuit 130. The operations regarding the control unit 140 will be explained in FIG. 4.

According to the embodiment of the present disclosure, the communication circuit 150 may be used for communicating with the external control device 200. The communication circuit 150 may transmit the instructions or signals received by the external control device 200 to the control unit 140, and transmit the data measured by the electrical stimulation device 100 to the external control device 200. According to the embodiment of the present disclosure, the communication circuit 150 may be a wireless communication or a wire communication for communicating with the external control device 200.

According to an embodiment of the present disclosure, all the electrodes of the electrical stimulation device 100 may be activated during the electrical stimulation. Therefore, users do not need to select which electrodes to be activated, and do not need to select which activated electrodes are negative polarity or positive polarity. For example, if the electrical stimulation device 100 is equipped with 8 electrodes, these 8 electrodes can be 4 positive polarities and 4 negative polarities staggeringly arranged.

A pulse signal that is lower (e.g., 10K Hertz) than conventional electrical stimulation may be prone to cause discomfort such as the feeling of stabbing pain, or paresthesia to the user. In an embodiment of the present disclosure, the electrical stimulation signal is a high frequency (e.g., 500K Hertz) pulse signal, so it will not cause paresthesia to users, or just cause extremely slight paresthesia to users.

According to the embodiment of the present disclosure, the storage unit 160 may be a volatile memory (e.g., a random access memory (RAM)), or a non-volatile memory (e.g., flash memory), a read only memory (ROM), a hard drive, or any combination thereof. The storage unit 160 may be used for storing the files and data required for performing the electrical stimulation. According to an embodiment of the present disclosure, the storage unit 160 may be used for storing related information of the lookup table provided by the external control device 200.

Figure 4:
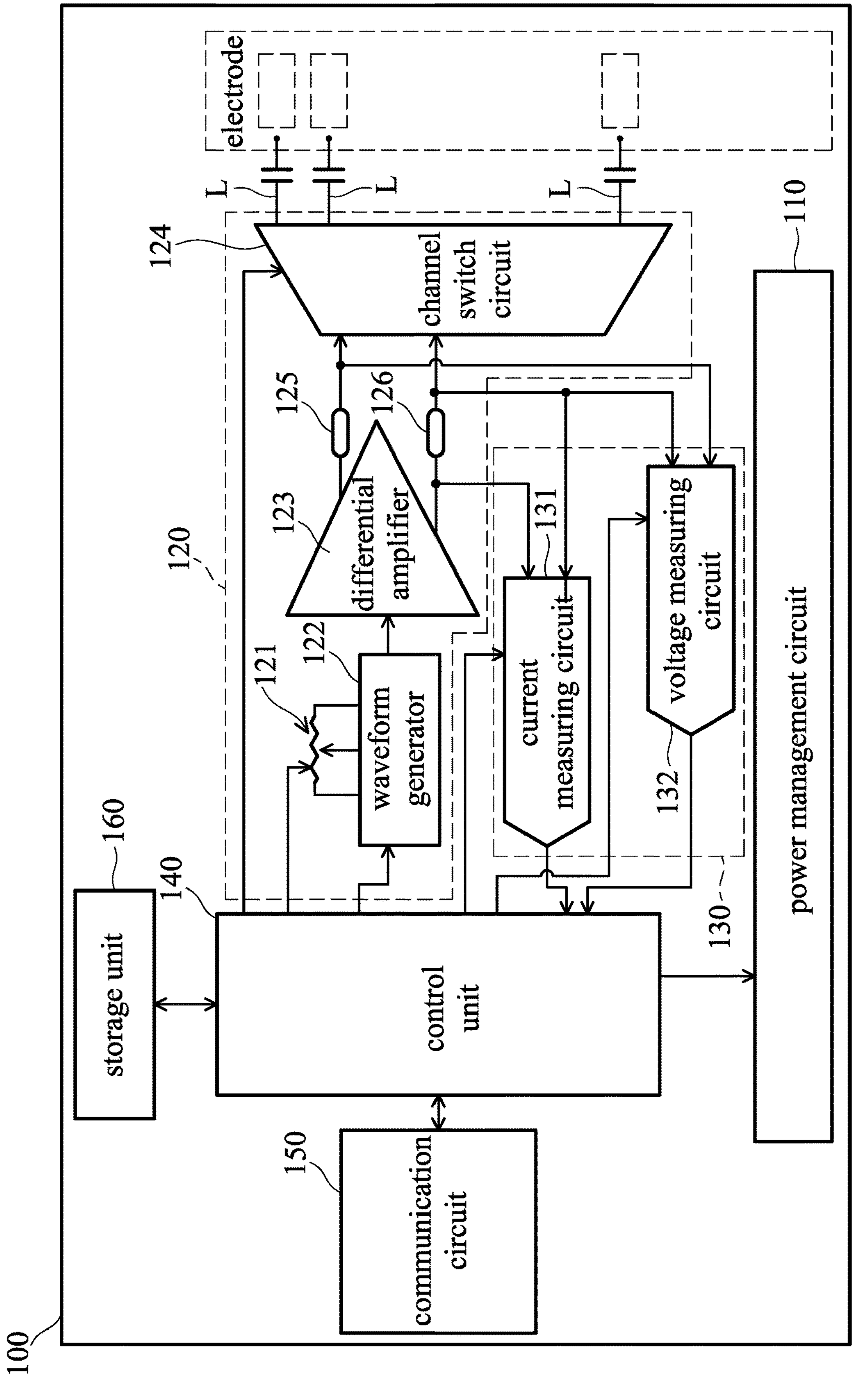
FIG. 4 is a detailed schematic diagram of an electrical stimulation device, according to an embodiment of the present disclosure.

FIG. 4 is a schematic diagram of an electrical stimulation device 100, according to an embodiment of the present disclosure. As shown in FIG. 4, the electrical stimulation signal generation circuit 120 may include a variable resistor 121, a waveform generator 122, a differential amplifier 123, a channel switch circuit 124, a first resistor 125, and a second resistor 126. The measuring circuit 130 may include a current measuring circuit 131 and a voltage measuring circuit 132. It should be appreciated that the schematic diagram shown in FIG. 4 is only for the convenience to explain the embodiments of the present disclosure, but the present disclosure is not limited to FIG. 4. The electrical stimulation device 400 may also include other elements, or other equivalent circuits.

As shown in FIG. 4, according to the embodiment of the present disclosure, the variable resistor 121 may be coupled to a serial peripheral interface (SPI) (not shown in the figure) of the control unit 140. The control unit 140 may transmit instructions to the variable resistor 121 via the SPI to adjust the resistance of the resistor 121, so as to adjust the amplitude of the electrical stimulation signal to be output. The waveform generator 122 may be coupled to a pulse width modulation (PWM) signal generator (not shown in the figure) of the control unit 140. The PWM signal generator may generate a square wave signal, and transmit the square wave signal to the waveform generator 122. After receiving the square wave signal generated by the PWM signal generator, the waveform generator 122 will convert the square wave signal into a sinusoidal wave signal, and transmit the sinusoidal wave signal to the differential amplifier 123. The differential amplifier 123 may convert the sinusoidal wave signal into a differential signal (i.e., the electrical stimulation signal output), and transmit the differential signal to the channel switch circuit 124 via the first resistor 125 and the second resistor 126. The channel switch circuit 124 may transmit the differential signal (i.e., the electrical stimulation signal output) to the electrode corresponding to each channel via the lead L in turn according to the instructions of the control unit 140.

As shown in FIG. 4, according to the embodiment of the present disclosure, the current measuring circuit 131 and the voltage measuring circuit 132 may be coupled to the differential amplifier 123, so as to obtain the current value and the voltage value of the differential signal (i.e., the electrical stimulation signal output). Besides, the current measuring circuit 131 and the voltage measuring circuit 132 may be used for measuring the voltage value and the current value on the tissues in the target area of the body of the user or the patient. In addition, the current measuring circuit 131 and the voltage measuring circuit 132 may be coupled to the input/output (I/O) interface (not shown in the figure) of the control unit 140, so as to receive the instructions from the control unit 140. According to the instructions of the control unit 140, the current measuring circuit 131 and the voltage measuring circuit 132 may adjust the current and the voltage of the electrical stimulation signal into a current value and a voltage value suitable for the control unit 140. For example, if the voltage value measured by the voltage measuring circuit 132 is ±10V, and the control unit 140 is suitable for processing a voltage value with 0-3 Volts, then the voltage measuring circuit 132 may decrease the voltage value to +1.5V, and then increase the voltage value to 0-3V.

After adjusting the current value and the voltage value, the current measuring circuit 131 and the voltage measuring circuit 132 may transmit the adjusted electrical stimulation signal to the analog-to-digital convertor (ADC) (not shown in the figure) of the control unit 140. The ADC may take samples from the electrical stimulation signal for the control unit to perform follow-up computation and analysis.

According to an embodiment of the present disclosure, when performing electrical stimulation on the target area of the body of a patient, the user (medical personnel or the patient himself) may select an electrical stimulation level from among a plurality of electrical stimulation levels on the operation interface of the external control device 200. In the embodiment of the present disclosure, different electrical stimulation levels may correspond to different target energies. The target energy may be a set of default energy. When the user selects an electrical stimulation level, the electrical stimulation device 100 may find out how many millijoules of energy must be provided to the target area in order to perform the electrical stimulation, according to the target energy corresponding to the electrical stimulation level selected by the doctor or the user. According to the embodiment of the present disclosure, in the trial phase, a plurality of target energies corresponding to a plurality of electrical stimulation levels may be regarded as a first set of default target energy. According to the embodiment of the present disclosure, the first set of the default target energy (i.e., the target energies) may be a linear sequence, an arithmetic sequence, or a geometric sequence, but the present disclosure is not limited thereto.

According to an embodiment of the present disclosure, in the trial phase, the external control device 200 may be provided with a lookup table. In this embodiment, the first lookup table may record each of the electrical stimulation levels and the corresponding target energy. Therefore, according to the electrical stimulation level selected by the user, the external control device 200 may look up the lookup table, and obtain the target energy corresponding to the electrical stimulation level selected by the user from the first target energy set. After obtaining the target energy corresponding to the electrical stimulation level selected by the user, the external control device 200 will transmit the target energy to the electrical stimulation device 100. Thus, the electrical stimulation device 100 may perform electrical stimulation on the target area according to the target energy.

According to another embodiment of the present disclosure, the electrical stimulation device 100 may be provided with a built-in first lookup table (e.g., a first lookup table stored in the storage unit 160). In this embodiment, the first lookup table may record each of the electrical stimulation levels and the corresponding target energy. After the user has selected an electrical stimulation level from the external control device, the external control device 200 will transmit an instruction to inform the control unit 140 of the electrical stimulation device 100 what electrical stimulation level was selected by the user. Then, the control unit 140 may select the target energy that corresponds to the electrical stimulation level selected by the user from the first target energy set according to the built-in first lookup table. After obtaining the target energy, the electrical stimulation device 100 may perform electrical stimulation on the target area according to the selected target energy, until the corresponding first target energy is transmitted to the target area and the time for the electrical stimulation ends. One round of electrical stimulation is thus completed.

According to another embodiment of the present disclosure, the communication circuit 150 may first obtain the electrical stimulation level selected by the user, and the first lookup table, from the external control device 200. In this embodiment, the first lookup table may record the electrical stimulation level and the corresponding target energy. Then, the control unit 140 selects the target energy that corresponds to the electrical stimulation level selected by the user from the first target energy set, according to the electrical stimulation level selected by the user and the first lookup table that are obtained from the external control device 200. After obtaining the target energy, the electrical stimulation device 100 may thus perform electrical stimulation on the target area according to the target energy.

According to the embodiment of the present disclosure, the user may select the electrical stimulation level from the lowest level (the lowest level of electrical stimulation corresponds to the lowest target energy in the first target energy set). After the electrical stimulation ends and the limited period passes, the next target energy may be selected from the first target energy set. Once the user finds the target energy that he/she prefers or that is more therapeutically effective, then the target energy may be regarded as a predetermined target energy, and the electrical stimulation level corresponding to the predetermined target energy may be regarded as a predetermined electrical stimulation level.

According to an embodiment of the present disclosure, in the permanent implantation phase, the external control device 200 (e.g., a controller of the external control device 200) may select a target energy upper bound and a target energy lower bound from the first target energy set according to the predetermined electrical stimulation level. Then, the external control device 200 (e.g., a controller of the external control device 200) may generate a second target energy set according to the target energy upper bound and the target energy lower bound. In this embodiment, the external control device 200 (e.g., a controller of the external control device 200) may generate a second lookup table according to the electrical stimulation level corresponding to each of the target energies in the second target energy set. The external control device 200 may transmit the second lookup table and the related parameter information to the electrical stimulation device 100. When the user is operating the external control device 200, the electrical stimulation device 100 may perform electrical stimulation according to the second lookup table and the related parameter information. According to an embodiment of the present disclosure, in the trial phase, an external electrical stimulation device (i.e., a non-implantable electrical stimulation device) is used to perform electrical stimulation according to the first target energy set in the first lookup table selected by the user. In the permanent phase, the electrical stimulation device 100 (i.e., an implantable electrical stimulation device) is used to perform electrical stimulation according to the second target energy set in the second lookup table selected by the user. In an embodiment of the present disclosure, the electrical stimulation device 100 performs electrical stimulation on the target area, until the corresponding second target energy is transmitted to the target area and this round of electrical stimulation ends. One round of electrical stimulation is thus completed.

According to another embodiment of the present disclosure, in the permanent implantation phase, the electrical stimulation device 100 may select a target energy upper bound and a target energy lower bound from the first target energy set according to the predetermined electrical stimulation level. Then, the electrical stimulation device 100 may generate the second target energy set according to the target energy upper bound and the target energy lower bound. In this embodiment, the electrical stimulation device 100 may generate a second lookup table according to the second target energy set and the electrical stimulation level corresponding to each of the target energies in the second target energy set. The electrical stimulation device 100 may transmit the second lookup table and the related parameter information to the external control device 200. When the user is operating the external control device 200, the electrical stimulation device 100 may perform electrical stimulation according to the second lookup table and the related parameter information.

According to the embodiment of the present disclosure, the second target energy set may be a linear sequence, an arithmetic sequence, or a geometric sequence, but the present disclosure is not limited thereto. According to an embodiment of the present disclosure, the number of the target energies included by the first target energy set may be the same as the number of the target energies included by the second target energy set. According to another embodiment of the present disclosure, the number of the target energies included by the first target energy set may be different to the number of the target energies included by the second target energy set.

Figure 5A:
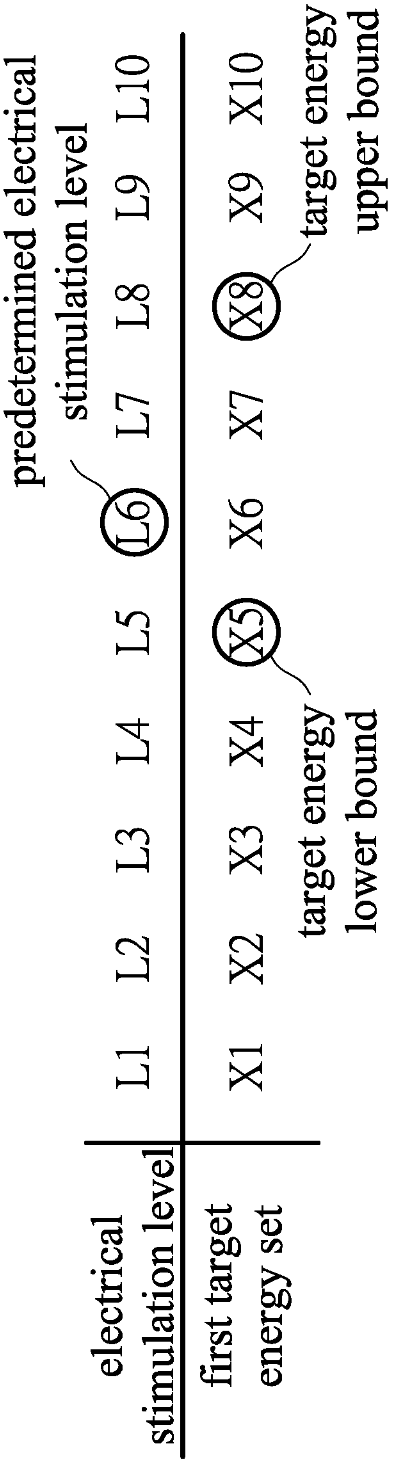
FIG. 5A illustrates the first target energy set, according to an embodiment of the present disclosure.
Figure 5B:
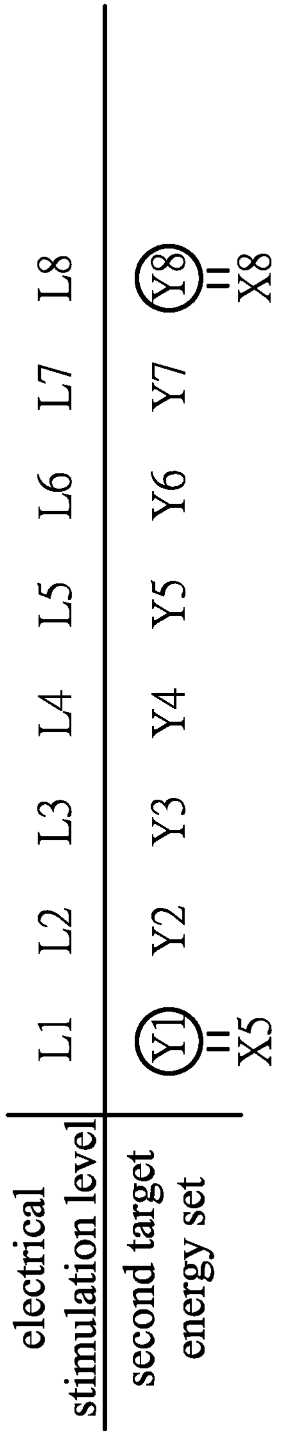
FIG. 5B illustrates the second target energy set, according to an embodiment of the present disclosure.

FIG. 5A illustrates the first target energy set, according to an embodiment of the present disclosure. FIG. 5B illustrates the second target energy set, according to an embodiment of the present disclosure. It should be appreciated that FIG. 5A and FIG. 5B are only for depicting an embodiment of the present disclosure, but the present disclosure is not limited to the first target energy set and the second target energy set in FIG. 5A and FIG. 5B.

As shown in FIG. 5A, the first lookup table may store the correspondence between electrical stimulation levels and the first target energies. The first target energy set may include the target energy X1-X10. The electrical stimulation level Level 1 (L1)-Level 10 (L10) correspond to the target energies X1-X10 respectively, and the unit of the target energy is millijoule. In addition to the target energies, the electrical stimulation levels L1-L10 may further corresponds to different current values or voltage values. In this embodiment, in the trial phase, when the predetermined electrical stimulation level selected by the user is L6 (the predetermined target energy is X6, accordingly), the predefined target energy upper bound is X8 and the target energy lower bound is X5. There is a target energy between the target energy upper bound X8 and the predetermined target energy X6, while there is no target energy between the target energy lower bound X5 and the predetermined target energy X6.

In the permanent implantation phase, after obtaining the target energy upper bound X8 and the target energy lower bound X5, the electrical stimulation device 100 or the external control device 200 may generate the second target energy set according to the target energy upper bound X8 and the target energy lower bound X5. As shown in FIG. 5B, the second target energy set may include target energies Y1-Y8, which correspond to the electrical stimulation levels L1-L8 of the external control device 200 respectively. Besides, in this embodiment, the lowest target energy Y1 of the second target energy set equals to the target energy lower bound X5, and the highest target energy Y8 equals to the target energy upper bound X8. In the permanent implantation phase, the electrical stimulation device 100 and the external control device 200 may perform operations of electrical stimulation according to the second target energy set.

According to the embodiment of the present disclosure, when corresponding to a predetermined electrical stimulation level in the trial phase, the first target energy set may include a target energy upper bound and a target energy lower bound. The target energy upper bound and the target energy lower bound will be brought into the permanent implantation phase. The target energy upper bound will be the highest target energy in the second target energy set, and the target energy lower bound will be the lowest target energy in the second target energy set (as shown in FIG. 5B). As such, the user may perform the electrical stimulation in the permanent implantation phase using an energy intensity near the predetermined electrical stimulation level selected, thus the safety of the electrical stimulation is further assured.

According to an embodiment of the present disclosure, there is a first number of target energies between the target energy upper bound and the predetermined target energy, and there is a second number of target energies between the target energy lower bound and the predetermined target energy. According to an embodiment of the present disclosure, the first number (e.g., 2) is larger than the second number (e.g., 1) (as shown in FIG. 5). According to another embodiment of the present disclosure, the first number may be equivalent to the second number.

According to an embodiment of the present disclosure, the predetermined target energy is not included in the second target energy set (as shown in FIG. 5B). According to another embodiment of the present disclosure, the predetermined target energy may be included in the second target energy set.

According to an embodiment of the present disclosure, the trial phase and the permanent implantation phase may both be further divided into a non-electrically-stimulating phase and an electrically-stimulating phase. In other words, the trial phase may include the non-electrically-stimulating phase and the electrically-stimulating phase, and the permanent implantation phase may also include the non-electrically-stimulating phase and the electrically-stimulating phase. The non-electrically-stimulating phase refers to when the electrical stimulation device 100 and the external control device 200 have just been turned on, or after the electrical stimulation device 100 and the external control device 200 have been connected, but the user has not yet initiated electrical stimulation. The electrical-stimulating phase refers to when the electrical stimulation device 100 has started providing electrical stimulation treatment.

Figure 6:
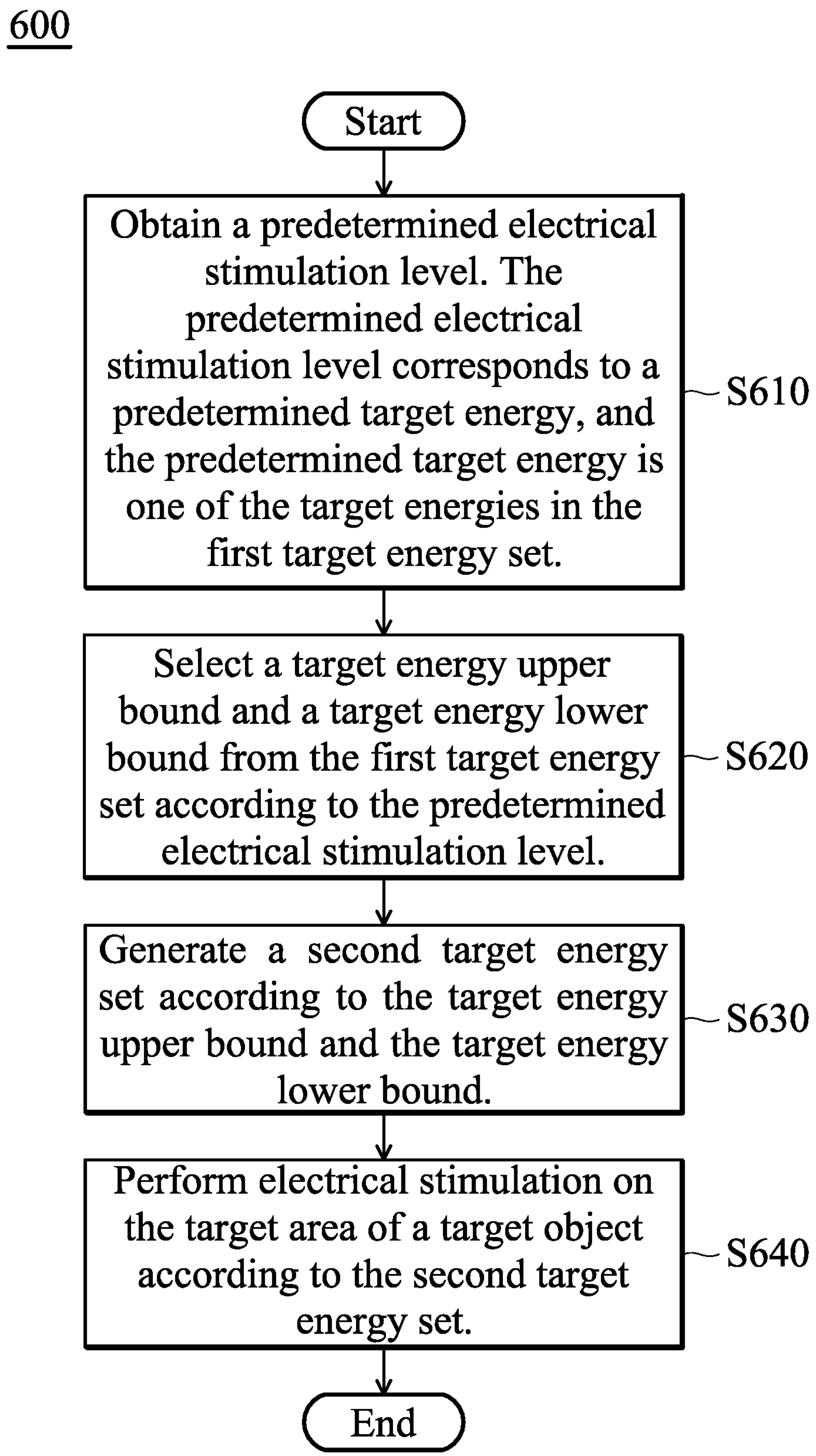
FIG. 6 is a flow diagram of the electrical stimulation method, according to an embodiment of the present disclosure.

FIG. 6 is the flow diagram 600 of an electrical stimulation method, according to an embodiment of the present disclosure. The flow diagram 600 of the electrical stimulation method is applied to the electrical stimulation device 100 and the external control device 200. As shown in FIG. 6, in step S610, a predetermined electrical stimulation level is obtained by the electrical stimulation device 100 or the external control device 200. The predetermined electrical stimulation level corresponds to a predetermined target energy, and the predetermined target energy is one of the target energies in the first target energy set.

In step S620, a target energy upper bound and a target energy lower bound are selected from the first target energy set according to the predetermined electrical stimulation level by the electrical stimulation device 100 or the external control device 200.

In step S630, a second target energy set is generated according to the target energy upper bound and the target energy lower bound by the electrical stimulation device 100 or the external control device 200.

In step S640, electrical stimulation is performed on the target area of a target object (i.e., the patient) according to the second target energy set by the electrical stimulation device 100.

According to an embodiment of the present disclosure, in the electrical stimulation method, the first target energy set is a sequence of numbers. Additionally, a first number of target energies are between the predetermined target energy and the target energy upper bound, and a second number of target energies are between the predetermined target energy and the target energy lower bound. According to an embodiment of the present disclosure, in the electrical stimulation method, the first number may be equivalent to the second number. According to another embodiment of the present disclosure, in the electrical stimulation method, the first number may not be equivalent to the second number.

According to an embodiment of the present disclosure, in the electrical stimulation method, the first target energy set may be a linear sequence, an arithmetic sequence, or a geometric sequence, but the present disclosure is not limited thereto.

According to an embodiment of the present disclosure, in the electrical stimulation method, the second target energy set may include the target energy upper bound and the target energy lower bound. According to an embodiment of the present disclosure, in the electrical stimulation method, the second target energy set may include the predetermined target energy, the target energy upper bound, and the target energy lower bound.

According to an embodiment of the present disclosure, in the electrical stimulation method, the target energy upper bound is the highest target energy in the second target energy set, and the target energy lower bound is the lowest target energy in the second target energy set.

According to an embodiment of the present disclosure, in the electrical stimulation method, the second target energy set may be a linear sequence, an arithmetic sequence, or a geometric sequence, but the present disclosure is not limited thereto.

According to an embodiment of the present disclosure, a computer-readable storage medium may store one or more instructions, and cooperate with the electrical stimulation device 100 and the external control device 200. When the instructions stored by the computer-readable storage medium are executed by the electrical stimulation device 100, the electrical stimulation device 100 and the external control device 200 may execute a plurality of steps included by the electrical stimulation method.

According to the electrical stimulation method provided by the present disclosure, at the beginning, users may select a predetermined target energy from the first target energy. Then, the electrical stimulation device 100 or the external control device 200 may generate the second target energy set for subsequent electrical stimulation operations according to the predetermined electrical stimulation level that corresponds to the predetermined target energy. Therefore, a set of target energies that are more suitable for the patient may be found out by using the electrical stimulation method provided by the present disclosure.

Ordinal terms used in the claims, such as "first," "second," "third," etc., are only for convenience of explanation, and do not imply any precedence relation between one another.

The steps of the methods and algorithms provided in the present disclosure may be directly applied to a hardware and a software module or the combination thereof by executing a processor. A software module (including executing instructions and related data) and other data may be stored in a data memory, such as random access memory (RAM), flash memory, read-only memory (ROM), erasable programmable read only memory (EPROM), electrically erasable programmable read only memory (EEPROM), registers, hard drives, portable drives, CD-ROM, DVD, or any other computer-readable storage media format in the art. For example, a storage media may be coupled to a machine device, such as a computer/processor (denoted by "processor" in the present disclosure, for the convenience of explanation). The processor may read information (such as codes) from and write information to a storage media. A storage media may integrate a processor. An application-specific integrated circuit (ASIC) includes the processor and the storage media. A user apparatus includes an ASIC. In other words, the processor and the storage media are included in the user apparatus without directly connecting to the user apparatus. Besides, in some embodiments, any product suitable for computer programs includes a readable storage media, wherein the storage media includes codes related to one or more disclosed embodiments. In some embodiments, the computer program product may include packaging materials.

The above paragraphs are described with multiple aspects. Obviously, the teachings of the specification may be performed in multiple ways. Any specific structure or function disclosed in examples is only a representative situation. According to the teachings of the specification, it should be noted by those skilled in the art that any aspect disclosed may be performed individually, or that more than two aspects could be combined and performed.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An electrical stimulation method, applied to an electrical stimulation device and an external control device, comprising:

obtaining a predetermined electrical stimulation level using the external control device, wherein the predetermined electrical stimulation level corresponds to a predetermined target energy, and the predetermined target energy is one of a plurality of target energies in a first target energy set used in a trial phase;

selecting a target energy upper bound and a target energy lower bound from the first target energy set according to the predetermined electrical stimulation level using the external control device, wherein the predetermined electrical stimulation level is between the target energy upper bound and the target energy lower bound;

generating a second target energy set according to the target energy upper bound and the target energy lower bound using the external control device, wherein the second target energy set is used in a permanent implantation phase; and performing electrical stimulation on a target area of a target object according to the second target energy set using the electrical stimulation.

2. The electrical stimulation method as claimed in claim 1, wherein the first target energy set is a sequence of numbers, a first number of target energies are between the predetermined target energy and the target energy upper bound, and a second number of target energies are between the predetermined target energy and the target energy lower bound.

3. The electrical stimulation method as claimed in claim 1, wherein the second target energy set includes the target energy upper bound and the target energy lower bound.

4. The electrical stimulation method as claimed in claim 1, wherein the target energy upper bound is the highest target energy in the second target energy set, and the target energy lower bound is the lowest target energy in the second target energy set.

5. The electrical stimulation method as claimed in claim 1, wherein the target area is spine, spinal nerve, vagus nerve, trigeminal nerve, lateral recess, or peripheral nerve.

6. The electrical stimulation method as claimed in claim 1, wherein the first target energy set is used in the trial phase in which electrical stimulation is performed on the target area of the target object according to the first target energy set using an external electrical stimulation device, and the second target energy set is used in the permanent implantation phase in which electrical stimulation is performed on the target area of the target object according to the second target energy set using the electrical stimulation device; and wherein the electrical stimulation device is implantable.

7. An electrical stimulation device, applied to perform electrical stimulation, comprising:

a controller, for obtaining a predetermined electrical stimulation level, wherein the predetermined electrical stimulation level corresponds to a predetermined target energy, and the predetermined target energy is one of the target energies in the first target energy set used in a trial phase;

wherein the controller selects a target energy upper bound and a target energy lower bound from the first target energy set according to the predetermined electrical stimulation level, and the controller generates a second target energy set according to the target energy upper bound and the target energy lower bound, wherein the predetermined electrical stimulation level is between the target energy upper bound and the target energy lower bound, and the second target energy set is used in a permanent implantation phase; and wherein the controller performs electrical stimulation on the target area according to the second target energy set.

8. The electrical stimulation device as claimed in claim 7, wherein the first target energy set is a sequence of numbers, a first number of target energies are between the predetermined target energy and the target energy upper bound, and a second number of target energies are between the predetermined target energy and the target energy lower bound.

9. The electrical stimulation device as claimed in claim 7, wherein the second target energy set includes the target energy upper bound and the target energy lower bound.

10. The electrical stimulation device as claimed in claim 7, wherein the target energy upper bound is the highest target energy in the second target energy set, and the target energy lower bound is the lowest target energy in the second target energy set.

11. The electrical stimulation device as claimed in claim 7, wherein the target area is spine, spinal nerve, vagus nerve, trigeminal nerve, lateral recess, or peripheral nerve.

12. An external control device, applied to perform electrical stimulation, comprising:

a controller, for obtaining a predetermined electrical stimulation level, wherein the predetermined electrical stimulation level corresponds to a predetermined target energy, and the predetermined target energy is one of target energies in a first target energy set used in a trial phase;

wherein the controller selects a target energy upper bound and a target energy lower bound from the first target energy set according to the predetermined electrical stimulation level, and the controller generates a second target energy set according to the target energy upper bound and the target energy lower bound, wherein the predetermined electrical stimulation level is between the target energy upper bound and the target energy lower bound, and the second target energy set is used in a permanent implantation phase; and wherein the external control device transmits the second target energy set to an electrical stimulation device, and the electrical stimulation device performs electrical stimulation on a target area according to the second target energy set.

13. The external control device as claimed in claim 12, wherein the first target energy set is a sequence of numbers, a first number of target energies are between the predetermined target energy and the target energy upper bound, and a second number of target energies are between the predetermined target energy and the target energy lower bound.

14. The external control device as claimed in claim 12, wherein the second target energy set includes the target energy upper bound and the target energy lower bound.

15. The external control device as claimed in claim 12, wherein the target energy upper bound is the highest target energy in the second target energy set, and the target energy lower bound is the lowest target energy in the second target energy set.

16. A computer-readable storage medium, storing one or more instructions, and cooperating with an electrical stimulation device and an external control device, and when the instructions are executed by the electrical stimulation device, the electrical stimulation device and the external control device execute a plurality of steps, comprising:

obtaining a predetermined electrical stimulation level, wherein the predetermined electrical stimulation level corresponds to a predetermined target energy, and the predetermined target energy is one of target energies in a first target energy set used in a trial phase;

selecting a target energy upper bound and a target energy lower bound from the first target energy set according to the predetermined electrical stimulation level, wherein the predetermined electrical stimulation level is between the target energy upper bound and the target energy lower bound and the second target energy set is used in a permanent implantation phase;

generating a second target energy set according to the target energy upper bound and the target energy lower bound; and performing electrical stimulation on a target area of a target object according to the second target energy set.

17. The computer-readable storage medium as claimed in claim 16, wherein the first target energy set is a sequence of numbers, a first number of target energies are between the predetermined target energy and the target energy upper bound, and a second number of target energies are between the predetermined target energy and the target energy lower bound.

18. The computer-readable storage medium as claimed in claim 16, wherein the second target energy set includes the target energy upper bound and the target energy lower bound.

19. The computer-readable storage medium as claimed in claim 16, wherein the target energy upper bound is the highest target energy in the second target energy set, and the target energy lower bound is the lowest target energy in the second target energy set.

20. The computer-readable storage medium as claimed in claim 16, wherein the target area is spine, spinal nerve, vagus nerve, trigeminal nerve, lateral recess, or peripheral nerve.

21. The computer-readable storage medium as claimed in claim 16, wherein the first target energy set is used in the trial phase in which electrical stimulation is performed on the target area of the target object according to the first target energy set using an external electrical stimulation device, and the second target energy set is used in the permanent implantation phase in which electrical stimulation is performed on the target area of the target object according to the second target energy set using the electrical stimulation device; and wherein the electrical stimulation device is implantable.

* * * * *